United States Patent [19]

Sasayama et al.

[11] Patent Number: 4,900,425
[45] Date of Patent: Feb. 13, 1990

[54] OXYGEN SENSOR

[75] Inventors: Takao Sasayama, Hitachi; Seikoh Suzuki, Hitachiota; Toshitaka Suzuki, Hitachi; Masayuki Miki; Sadayasu Ueno, both of Katsuta, all of Japan

[73] Assignee: Hitachi, Ltd., Tokyo, Japan

[21] Appl. No.: 597,030

[22] Filed: Apr. 5, 1984

[30] Foreign Application Priority Data

Apr. 6, 1983 [JP] Japan .................................. 58-59310

[51] Int. Cl.[4] ........................................... G01N 27/58
[52] U.S. Cl. .................................... 204/426; 204/406; 204/412; 204/424; 204/425
[58] Field of Search ................ 204/406, 412, 421, 424, 204/425, 426, 427, 428, 429

[56] References Cited

U.S. PATENT DOCUMENTS

| 4,107,019 | 8/1978 | Takao et al. ......................... 204/425 |
| 4,126,532 | 11/1978 | Takao et al. ......................... 204/426 |
| 4,272,329 | 6/1981 | Hetrick et al. ................... 204/412 X |
| 4,272,330 | 6/1981 | Hetrick et al. ................... 204/412 X |
| 4,272,331 | 6/1981 | Hetrick et al. ................... 204/412 X |
| 4,292,158 | 9/1981 | Muller et al. ......................... 204/426 |
| 4,298,573 | 11/1981 | Fujishiro ............................ 204/412 X |
| 4,302,312 | 11/1981 | Ishitani et al. ....................... 204/412 |
| 4,384,935 | 5/1983 | De Jong .............................. 204/426 |

Primary Examiner—Nam X. Nguyen
Attorney, Agent, or Firm—Antonelli, Terry & Wands

[57] ABSTRACT

An oxygen sensor is disclosed in which an airtight reference chamber isolated from a surrounding space is formed on one main surface of a solid electrolyte, a current is supplied to the solid electrolyte to pump out oxygen from the reference chamber in such a manner that oxygen in the reference chamber is ionized and then passes through the solid electrolyte, means is provided for transferring oxygen from the surrounding space to the reference chamber in such a manner that oxygen in the surrounding space is ionized and then passes through the solid electrolyte, and the oxygen concentration in the surrounding space is detected on the basis of the current supplied to the solid electrolyte.

7 Claims, 3 Drawing Sheets

OXYGEN SENSOR

The present invention relates to an oxygen sensor, and more particularly to an oxygen sensor suited to measure the oxygen concentration in the exhaust gas from a combustion chamber.

Such an oxygen sensor as described in a British Patent No. 1,523,550 has hitherto been used to measure the oxygen concentration in a gas. This oxygen sensor operates as follows. An exhaust gas is diffused from an orifice into a reference space, and oxygen contained in the exhaust gas is pumped out from the reference space by a pump cell which is made up of a reference electrode, a solid electrolyte, and a measuring electrode. At this time, the oxygen concentration in the exhaust gas is measured on the basis of a pump current flowing through the solid electrolyte. When the partial pressure of oxygen contained in the exhaust gas is expressed by $P_{o2}$, the pump current $I_p$ is given by the following formula:

$$I_p \simeq \frac{D \cdot A}{k \cdot T \cdot l} \cdot P_{o2} \quad (1)$$

where D indicates the diffusion constant of oxygen molecules, A the cross-sectional area of the orifice, k Boltzmann's constant, T an absolute temperature, and l the length of the orifice.

As can be seen from the above formula, in the conventional oxygen sensor, the pump current is dependent upon the diffusion rate of oxygen molecules passing through the orifice. Accordingly, when the orifice is blocked with dust or the like and thus the cross-sectional area of the orifice is varied, the measured value of the pump current (that is, the value of oxygen concentration) is varied.

It is accordingly an object of the present invention to provide an oxygen sensor in which there is no danger of dust or the like blocking gas flow.

In order to attain the above object, according to the present invention, there is provided an oxygen sensor which includes a solid electrolyte having an airtight reference chamber on one side thereof, a power source for supplying a current to the solid electrolyte to pump out oxygen from the reference chamber, and means for supplying oxygen to the reference chamber in such a manner that oxygen is ionized and then passes through the solid electrolyte, and in which the oxygen concentration in a space around the solid electrolyte is measured on the basis of the current supplied from the power source to the solid electrolyte.

The present invention will become more apparent from the following detailed description of embodiments taken in conjunction with the accompanying drawings, in which.

Now, embodiments of the present invention will be explained below in detail, with reference to the drawings.

Figure 1:
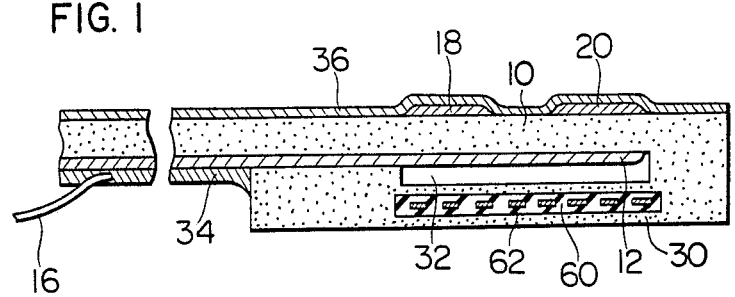
FIG. 1 is a sectional view showing the structure a main part of an embodiment of an oxygen sensor according to the present invention.
Figure 2:
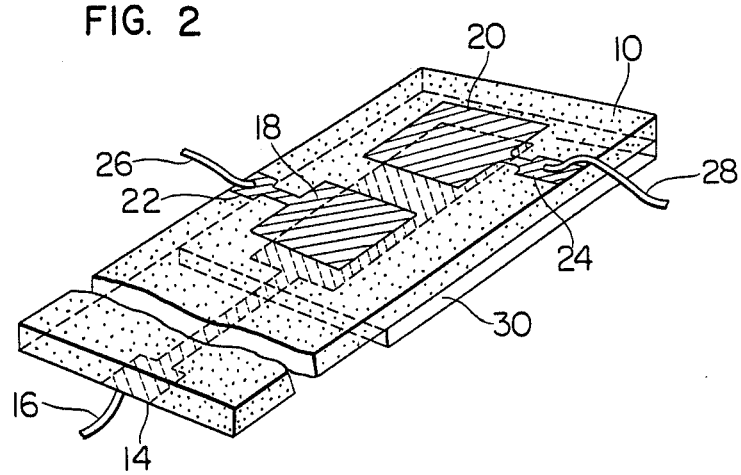
FIG. 2 is a perspective view of the main part shown in FIG. 1.

FIG. 1 is a sectional view showing a main part of an embodiment of an oxygen sensor according to the present invention, and FIG. 2 is a perspective view of the main part shown in FIG. 1.

Figure 3:
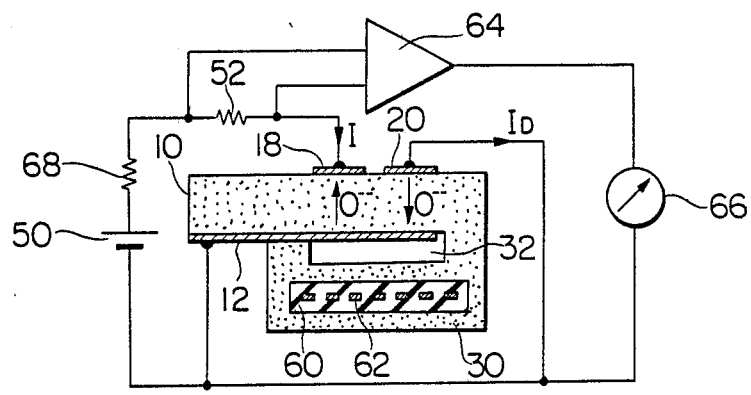
FIG. 3 is a circuit diagram of the embodiment shown in FIGS. 1 and 2.

Referring to FIGS. 1 and 2, a solid electrolyte 10 (for example, zirconia) has the form of a flat board, and an electrode 12 is formed on one main surface of the solid electrolyte 10. The electrode 12 is connected to a lead wire 16 through a conductor 14. Two electrodes 18 and 20 are formed on the other main surface of the solid electrolyte 10, and connected to lead wires 26 and 28 through conductors 22 and 24, respectively. The electrodes 12, 18, and 20 are made of an active material capable of acting as an oxidation-reduction catalyst, for example, platinum, and are made porous to have gas permeability. A zirconia cover 30 is placed on the electrode 12, to isolate the electrode 12 from the outside atmosphere. An airtight reference chamber 32 is formed between the electrode 12 and cover 30. The electrode 12 is coated with a protection layer 34, and the electrodes 18 and 20 are coated with a protection layer 36. An alumina layer 60 is provided in the cover 30, and a platinum heater 62 is buried in the alumina layer 60. As mentioned above, the cover 30 is made of the same material as the solid electrolyte 10. The solid electrolyte 10, cover 30, and alumina layer 60 are united in one body by sintering. The electrodes 12, 18, and 20 are connected to a power source 50 (having a voltage of 0.5 to 1 V) and a current measuring resistor 52, as shown in FIG. 3. As is clear from the structure, current paths, and oxygen ion flow shown in FIG. 3, for example, the current supplying means (e.g., 12, 18 and 50) continually pumps oxygen out of the reference chamber 32 while, simultaneously, oxygen continually is supplied to the reference chamber 32 from the surrounding space. In more detail, the positive and negative terminals of the power source 50 are connected to the electrodes 18 and 12, respectively, in order to supply a current I to the solid electrolyte 10. Owing to the current I, an oxygen molecule in the reference chamber 32 is ionized at the interface between the electrode 12 and the solid electrolyte 10. The oxygen ion thus formed is moved across the solid electrolyte 10, and again becomes an oxygen molecule at the electrode 18. That is, oxygen in the reference chamber 32 is pumped out. Accordingly, the oxygen partial pressure $P_{in}$ in the reference chamber 32 is decreased, and becomes different from the oxygen partial pressure $P_{out}$ of an exhaust gas existing in a surrounding space. An oxygen ion can be produced at each of the electrodes 20 and 12. However, owing to the above difference in oxygen partial pressure, the oxygen ion concentration obtained in the vicinity of the electrode 20 is different from that obtained in the vicinity of the electrode 12. Accordingly, as seen in FIG. 3, for example, simultaneously with the pumping out of oxygen from the reference chamber 32, oxygen diffuses into the chamber 32. Thus, an oxygen ion diffusion current $I_D$ flows through an external current path, since the electrodes 20 and 12 are connected to each other by means of lead wire. The diffusion current $I_D$ is given by the following equation:

$$I_D = C \cdot q \cdot A \cdot \Delta n \tag{2}$$

where C is a constant dependent upon electrode conditions, q the electronic charge, A the overlapping area of the electrodes 12 and 20, and $\Delta n$ a difference between the oxygen molecule density obtained in the vicinity of the electrode 20 and that obtained in the vicinity of the electrode 12.

When the oxygen molecule density obtained in the vicinity of the electrode 20 and that obtained in the vicinity of the electrode 12 are expressed by $n_{20}$ and $n_{12}$, respectively, the above difference $\Delta n$ is given by the following equation:

$$\Delta n = n_{20} - n_{12} \tag{3}$$

The oxygen partial pressures $P_{out}$ and $P_{in}$ are proportional to the oxygen molecule density $n_{20}$ and $n_{12}$, respectively. Accordingly, the difference $\Delta n$ in oxygen molecule density can be expressed as follows:

$$\Delta n \alpha P_{out} - P_{in} \tag{4}$$

That is, the equation (2) can be rewritten as follows:

$$I_D = C' \cdot q \cdot A \cdot (P_{out} - P_{in}) \tag{5}$$

where C' is the product of the constant C in the equation (2) and a proportional constant which is obtained from the formula (4).

When a sufficiently large current lying in a range less than an electronic conduction region is caused to flow through the solid electrolyte 10 by the power source 50, the oxygen partial pressure $P_{in}$ in the reference chamber 32 becomes for smaller than the oxygen partial pressure $P_{out}$ in the surrounding space, as indicated by the following formula:

$$P_{in} < P_{out} \tag{6}$$

Accordingly, the pump current I becomes equal to the diffusion current $I_D$, and thus takes a critical value. That is, the pump current I is expressed as follows:

$$I = C \cdot q \cdot A \cdot P_{out} \left( 1 - \frac{P_{in}}{P_{out}} \right) \tag{7}$$

$$\simeq C' \cdot q \cdot A \cdot P_{out} \tag{8}$$

In other words, oxygen is diffused from the outside of the solid electrolyte 10 into the reference chamber 32 in accordance with a difference in oxygen partial pressure between the surrounding space and the reference chamber 32, and the oxygen thus diffused is immediately pumped out from the reference chamber 32. The pump current at this time corresponds to the oxygen concentration in the surrounding space. The pump current I is converted by the resistor 52 into a voltage, and then amplified by an amplifier 64 to an appropriate level capable of showing the oxygen concentration on a meter 66. The temperature of the solid electrolyte 10 is controlled by the platinum heater 62 so as to be kept at a desired value. Incidentally, a resistor 68 is provided to make the voltage between the electrodes 12 and 18 less than a desired value over a wide range of supply current.

Figure 4:
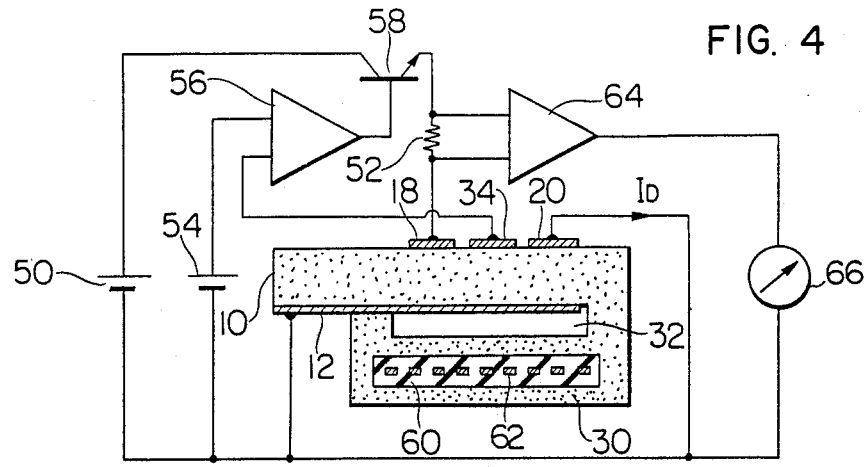
FIGS. 4 and 5 are circuit diagrams showing other embodiments of an oxygen sensor according to the present invention.

Another embodiment of an oxygen sensor according to the present invention will be explained below, with reference to FIG. 4. In FIG. 4, the same reference numerals as in FIG. 3 designate like parts. The embodiment shown in FIG. 4 is different from that shown in FIG. 3 in that a platinum electrode 34 is additionally provided. The electrode 34 is used for detecting an electromotive force e which is generated on the basis of a ratio of the oxygen partial pressure $P_{out}$ in the surrounding space to the oxygen partial pressure $P_{in}$ in the reference chamber 32. From Nernst's equation, we obtain the electromotive force e as follows:

$$e = \frac{R \cdot T}{4F} \ln \left( \frac{P_{out}}{P_{in}} \right) \tag{9}$$

where R is the gas constant, T an absolute temperature, and F the Faraday constant.

The electromotive force e is applied to one input terminal of an amplifier 56, and the other input terminal of the amplifier 56 is applied with a reference voltage $V_o$ from a power source 54. The reference voltage $V_o$ is put in a range from 0.3 to 0.5 V. The output of the amplifier 56 is applied to a controller 58 to control the pump current I so that the electromotive force e becomes equal to the reference voltage $V_o$. Thus, the electromotive force e is made equal to the reference voltage $V_o$, and therefore the following equation is obtained from the equation (9).

$$\frac{P_{out}}{P_{in}} = \exp \left( \frac{4F}{R \cdot T} \cdot V_o \right) = \text{const.} \tag{10}$$

From the equations (7) and (10), we obtain the following equation:

$$I = C \cdot q \cdot A \cdot P_{out} \left( 1 - \exp \left( \frac{4F}{R \cdot T} \cdot V_o \right) \right) \tag{11}$$

As can be seen from the equation (11), the pump current I can be made exactly proportional to the oxygen partial pressure $P_{out}$, without assuming the relation $P_{in} < P_{out}$ as in the formula (8). The pump current I is converted by the resistor 52 into a voltage, which is indicated, as the oxygen concentration, on the meter 66 in the same manner as in the embodiment shown in FIG. 3. Since the equation (11) contains an absolute temperature T, the pump current I is affected by temperature. However, a current supplied to the platinum heater 62 is controlled so that the temperature of the solid electrolyte 10 is kept constant, and therefore variations in the current I due to ambient temperature is negligibly small.

Figure 5:
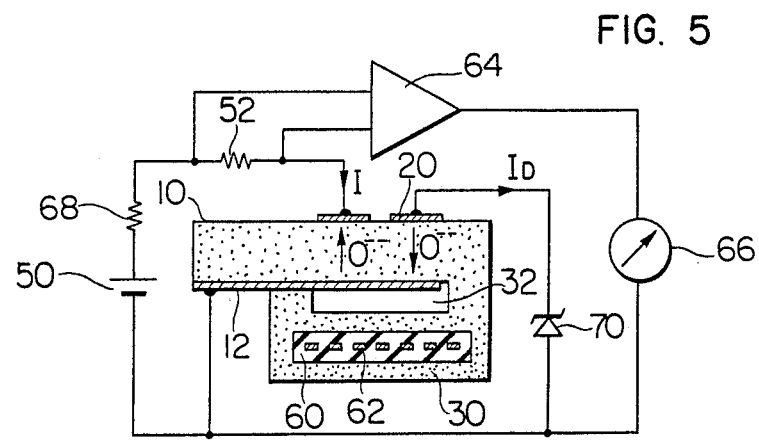
Figure 6:
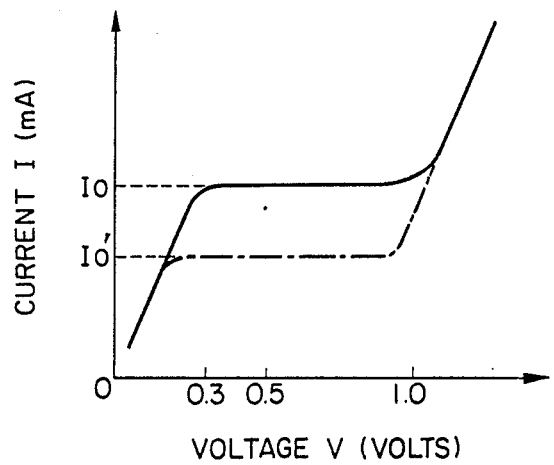
FIG. 6 is a graph for explaining the present invention.

FIG. 5 shows still another embodiment of an oxygen sensor according to the present invention, which is obtained by further improving the embodiment shown in FIG. 3. The embodiment shown in FIG. 5 is different from that shown in FIG. 3, in what a zener diode 70 is additionally provided. When a voltage is applied between the electrodes 12 and 18 by means of the power source 50, the pump current I flows through the solid electrolyte 10 in accordance with the applied voltage. When the applied voltage is low, the pump current I varies linearly with the applied voltage V, as shown in FIG. 6. When the applied voltage V is increased to about 0.3 V, the oxygen partial pressure $P_{in}$ in the reference chamber 32 is nearly equal to zero. That is, as can be seen from the equation (9), the electromotive force e becomes very large. Accordingly, the pump current $I_o$ is kept constant independently of an increase in applied voltage. However, when the applied voltage is increased to about 1 V, the solid electrolyte 10 is put in an electronic conduction state, that is, an electron can move through the solid electrolyte 10. Accordingly, the pump current I flows through the solid electrolyte in proportion to the applied voltage $V_o$. The pump current at a time when the electromotive force e has been abruptly increased, is the critical current $I_o$. When the oxygen partial pressure in the surrounding space is low, the critical current $I_o$ is decreased to a value $I_o'$, as indicated by a dot-dash line in FIG. 6.

In the embodiment shown in FIG. 5, the zener diode 70 has a zener voltage of 0.3 to 0.5 V. Accordingly, the diffusion current $I_D$ does not flow till the oxygen partial pressure $P_{in}$ in the reference chamber 32 is made equal to zero by the pump current which is supplied from the power source 50. When the oxygen partial pressure $P_{in}$ in decreased to zero, that is, when the pump current becomes equal to the critical current $I_o$, the electromotive force e appearing at the electrode 20 is abruptly increased, but the zener diode 70 prevents the electromotive force from increasing to an electronic conduction region. When the zener voltage of the diode 70 is made equal to $V_o$, the pump current is given by the equation (11), and thus the oxygen partial pressure $P_{out}$, that is, the oxygen concentration in the surrounding space can be precisely determined.

Figure 7:
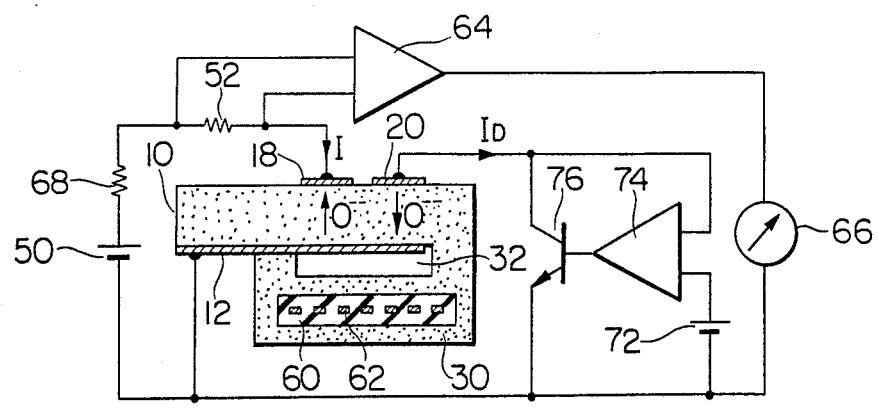
FIGS. 7 and 8 are circuit diagrams showing further other embodiments of an oxygen sensor according to the present invention.

FIG. 7 shows a further embodiment of an oxygen sensor according to the present invention which is a modified version of the embodiment shown in FIG. 5. In the embodiment shown in FIG. 7, a reference voltage source 72 having an output voltage of 0.3 to 0.5 V, an amplifier 74, and a transistor 76 are used in place of the zener diode 70 shown in FIG. 5. The amplifier 74 delivers an output which is proportional to a difference between the electromotive force e appearing at the electrode 20 and the reference voltage $V_o$ of the voltage source 72, when the electromotive force e is greater than the reference voltage $V_o$. The transistor 76 is applied with the output of the amplifier 74 to control the diffusion current $I_D$ so that the electromotive force e is equal to the reference voltage $V_o$.

Figure 8:
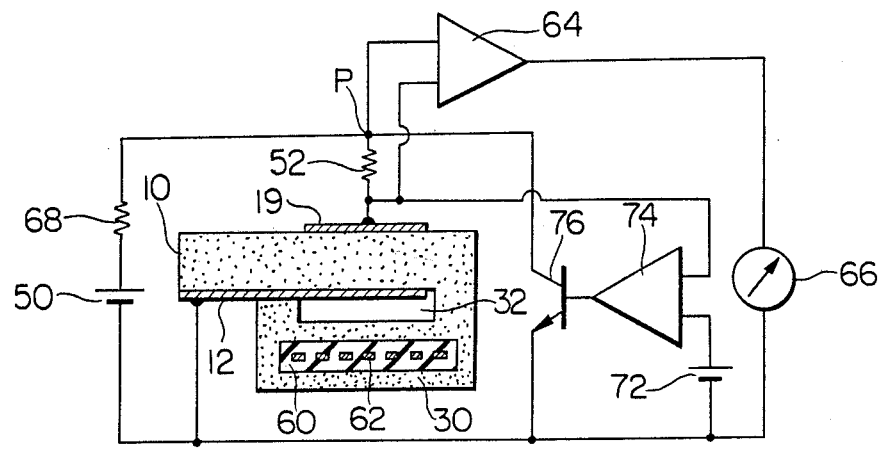
Figure 9:
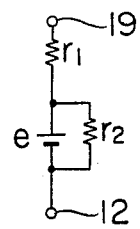
FIG. 9 is a circuit diagram showing the equivalent circuit of a solid electrolyte.

FIG. 8 shows still a further embodiment of an oxygen sensor according to the present invention. In this embodiment, a single electrode 19 is substituted for the electrodes 18 and 20 shown in FIG. 7. When the power source 50 causes a critical current to flow through the solid electrolyte 10 between the electrodes 12 and 19, the oxygen partial pressure $P_{in}$ in the reference chamber 32 is made equal to zero. Accordingly, a large electromotive force is generated between the electrodes 12 and 19. However, since the potential at a point P is limited by the reference voltage $V_o$ of the voltage source 72, the above electromotive force e cannot be greater than the reference voltage $V_o$. In more detail, if the electromotive force e becomes greater than the reference voltage $V_o$, the pump current will be made equal to zero, and the electromotive force e will immediately be decreased. Accordingly, the solid electrolyte 10 is kept at a stationary state, while having an electromotive force less than the reference voltage $V_o$. At this time, the solid electrolyte 10 can be expressed by an equivalent circuit shown in FIG. 9. The electromotive force e and resistance values $r_1$ and $r_2$ shown in FIG. 9 vary with the oxygen partial pressure $P_{out}$ in the surrounding space. Accordingly, the current flowing through the resistor 52 depends upon the oxygen partial pressure $P_{out}$. Further, in the embodiment shown in FIG. 8, a current corresponding to the diffusion current $I_D$ which flows through the zener diode 70 shown in FIG. 5, may be considered to flow through the solid electrolyte 10 on the basis of electronic conduction. Accordingly, the current I flowing through the resistor 52 shown in FIG. 8 is given by the equation (11).

We claim:
1. An oxygen sensor comprising:
   a solid electrolyte;
   a first active electrode provided on one of a pair of main surfaces of said solid electrolyte and having gas permeability;
   enclosing means for forming a reference chamber, said reference chamber being airtight to be isolated from a surrounding space, said reference chamber including therein at least a portion of said first electrode;
   a second active electrode and a third active electrode each provided on the other main surface of said solid electrolyte at a place opposite that portion of said first electrode which is included in said reference chamber, each of said second and third electrodes having gas permeability;
   a current path formed between said first electrode and said third electrode for continually supplying oxygen to said reference chamber in such a manner that oxygen in said surrounding space is ionized and then passes through said solid electrolyte;
   power supply means for continually supplying a current between said first electrode and said second electrode to continually pump out oxygen from said reference chamber in such a manner that oxygen in said reference chamber is ionized and then passes through said solid electrolyte, said power supply means and said current path being connected to the electrodes such that oxygen supplied from said surrounding space to said chamber is continually pumped out from said chamber, simultaneously with the supply of oxygen from the surrounding space, to maintain the oxygen partial pressure to be always far smaller in the chamber than the oxygen partial pressure in a space existing on the other main surface side of said solid electrolyte; and
   means for detecting the oxygen concentration in the space existing on the other main surface side of said solid electrolyte, on the basis of said current supplied by said power supply means.

2. An oxygen sensor according to claim 1, wherein said current path is a conductor electrically connecting the first and third electrodes.

3. An oxygen sensor according to claim 1, wherein said current path is a circuit for preventing an electromotive force produced between said first electrode and said third electrode from exceeding a predetermined value.

4. An oxygen sensor according to claim 3, wherein said current path includes a zener diode to prevent said electromotive force from exceeding the zener voltage of said diode.

5. An oxygen sensor according to claim 3, wherein said current path includes a reference voltage source generating a reference voltage equal to said predetermined value, and control means for controlling a current flowing between said first electrode and said third electrode so that said electromotive force is prevented from exceeding said reference voltage.

6. An oxygen sensor according to claim 1, further comprising a fourth active electrode having gas permeability and provided on the other main surface of said electrolyte at a place opposite that portion of said first electrode which is included in said reference chamber, and control means for controlling said current supplied by said power supply means so that an electromotive force produced between said first electrode and said fourth electrode has a predetermined value.

7. An oxygen sensor according to claim 1, wherein said power supply means and said current path are connected such that oxygen supplied from the surrounding space to said chamber is immediately pumped out from said chamber to maintain the oxygen partial pressure in the chamber at substantially zero.

* * * * *